United States Patent

Chang

[11] Patent Number: 5,779,682
[45] Date of Patent: Jul. 14, 1998

[54] NEEDLE GUARD TO PREVENT ACCIDENTAL NEEDLE STICKING

[76] Inventor: Steven C. Chang, 1000 Dove St., No. 250, Newport Beach, Calif. 92660

[21] Appl. No.: 905,637

[22] Filed: Aug. 4, 1997

[51] Int. Cl.⁶ .................................................. A61M 5/00
[52] U.S. Cl. ........................... 604/187; 604/263; 206/365
[58] Field of Search ........................... 604/187, 192, 604/263, 110; 206/364, 365

[56] References Cited

U.S. PATENT DOCUMENTS

| 4,742,910 | 5/1988 | Staebler ........................... 206/365 |
| 4,758,229 | 7/1988 | Doerschner ...................... 604/187 |
| 4,875,896 | 10/1989 | Kurtz .............................. 604/187 |
| 4,892,522 | 1/1990 | Suzuki et al. ................. 604/263 X |
| 5,209,733 | 5/1993 | Lever et al. ................... 206/366 X |
| 5,383,862 | 1/1995 | Berndt et al. ................... 604/187 |

*Primary Examiner*—John D. Yasko
*Attorney, Agent, or Firm*—Charles C. H. Wu

[57] ABSTRACT

A device for preventing needle sticking injuries to a user's finger or hand. The device is made of resin or a similar material having a hardened surface but flexible. The device can be formed as a circularly shaped plate or a polygon shaped plate. The plate has a plurality of angularly and radially outward slits placed at its center. The slits are designed to allow the penetration of a needle cap through the plate and provide a tight grip onto the needle cap and shields the needle users from sticking accidents and injuries.

9 Claims, 2 Drawing Sheets

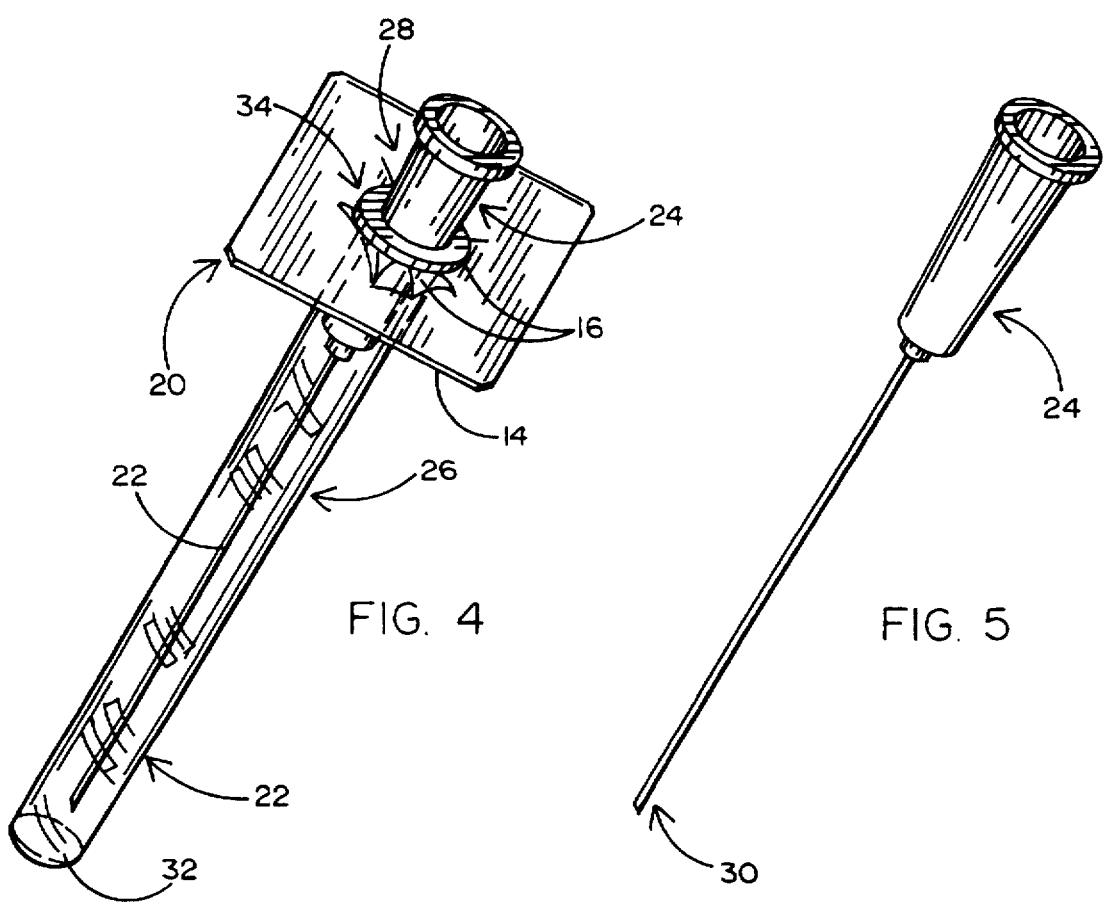

NEEDLE GUARD TO PREVENT ACCIDENTAL NEEDLE STICKING

BACKGROUND OF THE INVENTION

A common problem among doctors, nurses, and medical technicians occurs when trying to recap a needle. Because of the narrowness of the needle cap, the needle often misses the opening of the cap and punctures the finger of the user.

The present invention relates to a device that prevents the sticking of a needle into the tip of the thumb or forefinger when an user attempts to recap the needle. Specifically, after using needle and attempting to recap the needle, if the user misses the cap with the needle, the needle can puncture the user's skin. It is at this point that the sticking injury becomes most prevalent and most deadly because the used syringe needle may be contaminated and may contain deadly viruses such as HIV.

It is an object of this invention to provide a relatively inexpensive, simple and easy to use device to prevent or reduce the aforementioned sticking injury. It is inexpensive in the way that a large plastic board containing many pre-shaped needle guards can be manufactured with minimum costs. It is also easy to use in the way that the needle guards contained within the plastic board can be easily torn out similarly to tearing stamps off a large sheet of postage stamps.

Lastly, the needle guards are shaped to adapt to fit many different diameters of the commonly used needle caps. Therefore, this invention is broadly applicable for a wide variety of needles.

Currently on the market, there is not an easy to use and relatively inexpensive needle guard to prevent sticking injuries. Thus, there is a need for an easy-to-use and inexpensive needle guard to prevent sticking.

SUMMARY

The present invention meets this need by providing a protective plate that has multiple slits at its center. The slits allow the needle cap to penetrate through the needle guard at an angle perpendicular to the plane of the needle guard. The slits are formed in such a manner that a variety of sizes of needle caps can be slipped through said needle guard.

One aspect of the present invention is that the needle guard is provided for use with the style of needle which has needle cap with a small mouth opening at one end and a closed end at the other end. The needle typically has a sharp needle tip. The needle guards originate from a sheet of flexible material with a hardened surface having a plurality of perforations laid out to form rows and columns of needle guards. The perforations are adapted to allow easy tearing off of the needle guards. The tearing off of the needle guards are similar to the tearing off of stamps from a sheet of postage stamps.

The needle guards have a center portion. The center portion includes a plurality of slits extending outwardly and radially from the center portion of the needle guard to allow a needle cap to penetrate through the needle guards and to grip on to the needle cap.

For maximum protection, the needle guards are placed up against the lip of the needle cap opening and not at the base or the middle of the needle cap. Therefore, if a misdirected needle tip is projected toward the user's hand and fingers, the needle guards shield users', hands and fingers and protects the user from sticking injuries.

The sheet of flexible material with a hardened surface can be made of plastic or a polycarbonate material with the following characteristics: (1) it has the required thickness so that a misdirected needle tip cannot penetrate through it; (2) it has the required surface elasticity so that when a needle tip strikes its surface, it will partially absorb the needle tip rather than deflecting it off its surface; and (3) it can sustain through a sterilization process without being deformed out of shape.

DRAWINGS

These and other features, aspects, and advantages of the present invention will become better understood with reference to the following description, appended claims and accompanying drawings, where:

FIG. 4 is a side view illustrating the insertion of a needle into a needle cap held by the needle guard; and FIG. 5 is an example of a needle having a sharp tip.

DETAILED DESCRIPTION OF THE PREFERRED EMBODIMENTS

Figure 1:
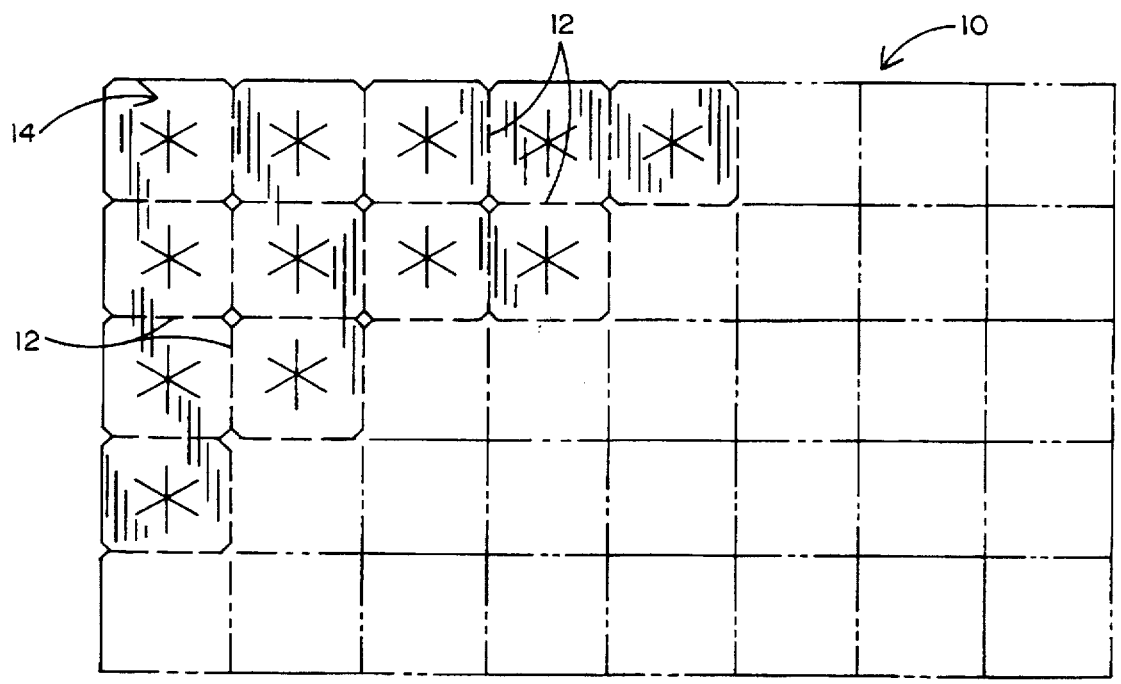
FIG. 1 is a view of a large plastic sheet containing many perforated needle guards similar to a sheet of postage stamps.

The present invention is targeted to a needle guard that is particularly suitable for preventing accidental needle sticking in the medical profession in connection to the ubiquitous hypodermic needle. With reference to FIGS. 1–5 of the drawings, FIG. 1 is a view of a sheet of needle guards 10 containing many needle guards 14. The design of the tear-off perforations 12 of the sheet of needle guards 10 is similar to a sheet of postage stamps. The sheet of needle guards 10 has a plurality of tear-off perforations 12 designed for tearing off pieces of needle guards 14. The size of the sheet of needle guards 10 can be any size that is economical to manufacture. It also should not be too large such that it would not fit inside of a typical medical office desk drawer or for that matter, it should not also be so large such that it would be more costly for a postal carrier to deliver the sheet of needle guards 10. Conversely, it should not be too small such that it would not offer adequate protection or economically, it is not cost effective to produce a few needle guards 14 at a time from the raw material. Ideally, the sizes of the sheets of needle guard 10 should be consistent with the sizes of the postal envelopes commonly available in office supplies stores.

Figure 2:
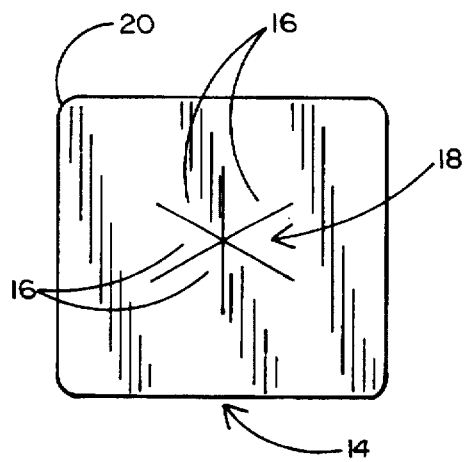
FIG. 2 is a top view of the needle guard.
Figure 3:
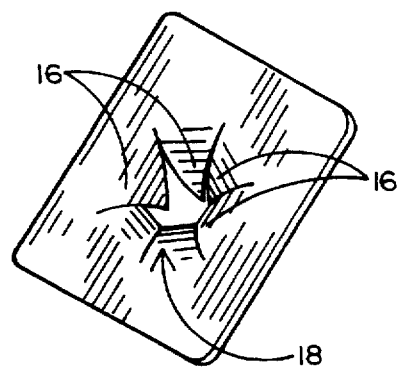
FIG. 3 is a bottom view of the slits after being perforated.

FIG. 2 is a detailed view of the needle guard 14 having a plurality of slits 16 at its center portion 18. The composition of the needle guard 14 has a certain stiffness and strength and a hardened surface such that the sharp tip 30 of the needle 24 cannot penetrate through the needle guard 14. Further, it has a certain elasticity and flexibility to allow its center portion 18 to flex out upon pressure and thus allowing the needle cap to be easily inserted through the center portion 18. Furthermore, at the same time the center portion 18 is adapted to tightly grip onto the surface of the needle cap 26.

The needle guard 14 can be pre-cut in the shape of a square. However, the shape of the needle guard 14 can be shaped into other configurations such as polygon, circular or elliptical shapes. If the needle guard 14 is shaped polygon, or squarely or rectangularly, then at its corners, the corners are tapered off to create rounded corners 20 for the purpose of rounding the sharp edges to prevent cutting or piercing the skin of the user of the invention.

At the center portion 18 of the needle guard 14, it has a plurality of angular spaced slits 16, each of which extends outwardly and radially from the center of the needle guard 14. The slits 16 allow the center portion 18 of the needle guard 14 to be pierced through by a needle cap 26 and concurrently maintaining a tight grip on the needle cap 26.

Taking into consideration of both the thickness and flexibility of the material used, the number of slits 16 and their dimensions are predetermined and pre-calculated to allow both easy penetration of the needle cap 26 and concurrently maintaining a tight grip on the needle cap 26 so it will not easily become detached from the needle guard 14.

FIGS. 4 and 5 show how the needle guard 14 is being used with a typical complete needle 22 having a needle 24, a needle cap 26, and a sharp tip 30. The needle cap 26 has a mouth 28 and a small lip 34 at one end and a closed end 32 at the other end. As shown in FIG. 5, when the cap 26 is removed, the sharp tip 30 of the needle 24 is exposed. It is recommended that the needle guard 14 be slid onto the needle cap 26 and pushed all the way up against the lip 34 of the needle cap for the first use of the complete needle 22.

To properly use the invention, before the needle 24 is taken out of the needle cap 26, the user places the needle guard 14 on the needle cap 26 by inserting the needle cap 26 portion of the complete needle 22 through the center portion 18 of the needle guard 14. The needle guard 14 is pushed up against the lip 34 of the needle cap 26. Having the needle guard 14 firmly gripping onto the needle cap 26, the needle 24 can be taken out of the complete needle 22 and be used accordingly.

After its use, the user may cap the needle 24 having the guard already in place. Firstly, the user's hands and fingers should be situated next to needle guard 14 and slide the needle guard 14 up against the lip 34 of the needle cap 26 for the purposes of maintaining the needle cap 26 in a stable position and for easier recap next time. Secondly, the user may now wish to cap the complete needle 22 by inserting the needle 24 through the mouth 28 of the needle cap 26. To guard against accidents, the needle guard 14 will shield the user's hands and fingers should the user accidentally misses the mouth 28 of the needle cap 26 with the needle 24. After the user realizes that he or she has missed the needle cap 26, the user may again try to insert the needle 20 into the needle cap 26. The needle 24 will stick into the needle guard 14 and can easily be pulled out. The user may again attempt to insert the needle 24 into the needle cap 26.

The preferred material for the sheet of needle guards 10 is a material that can be economically manufactured, preferably plastic. The material used for the sheet of needle guards 10 should be hypo-allergenic so that it can be used in a typical medical office.

In addition, the sheet of needle guards 10 can be made of plastic or a polycarbonate material having the following characteristics: (1) it has the required thickness so that a misdirected needle tip cannot penetrate through it; (2) it has the required surface elasticity so that when the sharp tip 30 of the needle strikes its surface, it will partially absorb the sharp tip 30 and stop the sharp tip 30 from deflecting and sliding off its surface; and (3) it can sustain through the sterilization process without being deformed.

What is claimed is:

1. A safety device for protecting and preventing users from sticking injuries in connection with the usage of needles, for use with needles having a needle cap with a mouth opening at one end and a closed end at the other end of the needle cap and having a sharp needle tip, comprising:

a sheet of flexible material having a firm surface further having a plurality of perforations laid out to form rows and columns of polygon shaped plates having round corners, said polygon shaped plates having round corners, said perforations are adapted to allow easy tearing off of the square plates using fingers, said polygon shaped plates each having a center portion, the center portion includes a plurality of slits extending outwardly and radially from the center of the polygon shaped plates for allowing the needle cap to penetrate through the slits and for gripping on to the needle cap, the needle cap having a lip at one end opposite the closed end, the polygon shaped plate is positioned abutting the lip of the needle cap whereby the polygon shaped plate shields the user's hands and fingers from accidental sticking injuries.

2. A safety device of claim 1 wherein the sheet of flexible material is made of plastic.

3. A safety device of claim 1 wherein the sheet of flexible material is made of polycarbonate.

4. A safety device of claim 1 wherein the polygon shaped plates are squarely shaped.

5. A safety device of claim 1 wherein the polygon shaped plates are rectangularly shaped.

6. A safety device for use with needles having a needle cap with a mouth opening at one end and a closed end at the other end for protecting and preventing users from sticking injuries in connection with the usage of needles, comprising:

a sheet of flexible material having a firm surface further having a plurality of perforations laid out to form rows and columns of circularly shaped plates, said perforations are adapted to allow tearing off of the circular plates using fingers and hands, said circularly shaped plates having a center portion, the center portion includes a plurality of slits extending outwardly and radially from the center of the circular plates for allowing the needle cap to penetrate through the slits and for gripping on to the needle cap securely, the circularly shaped plate is positioned abutting the lip of the needle cap whereby the polygon shaped plate shields the user's hands and fingers from accidental sticking injuries.

7. A safety device of claim 6 wherein the sheet of flexible material is made of plastic.

8. A safety device of claim 6 wherein the sheet of flexible material is made of polycarbonate.

9. A safety device of claim 6 wherein the circularly shaped plates are elliptically shaped.

* * * * *